United States Patent [19]

Rutsch et al.

[11] Patent Number: 5,368,985

[45] Date of Patent: Nov. 29, 1994

[54] BISACYLPHOSPHINE SULFIDES

[75] Inventors: Werner Rutsch; Gebhard Hug, Fribourg; Manfred Köhler, Freiburg, all of Switzerland

[73] Assignee: Ciba-Geigy Corporation, Ardsley, N.Y.

[21] Appl. No.: 203,858

[22] Filed: Feb. 28, 1994

Related U.S. Application Data

[63] Continuation of Ser. No. 925,239, Aug. 4, 1992, abandoned, which is a continuation of Ser. No. 819,320, Jan. 9, 1992, abandoned.

[30] Foreign Application Priority Data

Jan. 14, 1991 [CH] Switzerland .................... 84/91-2

[51] Int. Cl.$^5$ .................... C08F 2/50; C08F 4/00; C08G 59/17; G03F 7/029; C07F 9/53
[52] U.S. Cl. .................... 430/269; 430/288; 430/921; 430/923; 430/322; 522/17; 522/49; 522/50; 522/53; 522/64; 522/81; 522/103; 526/313; 546/21; 548/412; 549/5; 549/6; 549/216; 568/15
[58] Field of Search .................... 522/49, 64, 17, 50, 522/53; 430/322, 269, 288; 546/21; 548/412; 549/5, 6, 216; 568/15

[56] References Cited

U.S. PATENT DOCUMENTS

| | | | |
|---|---|---|---|
| 4,522,693 | 6/1985 | Henne | 522/104 |
| 4,737,593 | 4/1988 | Ellrich et al. | |
| 4,792,632 | 12/1988 | Ellrich et al. | |
| 4,945,032 | 7/1990 | Murphy | 430/322 |

FOREIGN PATENT DOCUMENTS 0047902  9/1980  European Pat. Off.
0184095  6/1986  European Pat. Off.

OTHER PUBLICATIONS

K. Issleif et al., Z. Anorg. Allg. Chem., 408, 266 (1974).
A. R. Barron, et al., J. Chem. Soc., Chem. Commun. 1987, 1753.

Primary Examiner—Marion E. McCamish
Assistant Examiner—Arthur H. Koeckert
Attorney, Agent, or Firm—Luther A. R. Hall

[57] ABSTRACT

Bisacylphosphine sulfides of formula I $$R_3-\overset{\overset{O}{\|}}{C}-\overset{\overset{S}{\|}}{\underset{\underset{R_1}{|}}{P}}-\overset{\overset{O}{\|}}{C}-R_2, \quad (I)$$

wherein $R_1$ is unsubstituted $C_1$–$C_{18}$ or $C_1$–$C_8$alkyl which is substituted by phenyl, —CN, $C_1$–$C_{12}$alkoxy or halogen, $C_2$–$C_{18}$alkenyl, unsubstituted $C_5$–$C_8$cycloalkyl or $C_5$–$C_8$cycloalkyl which is substituted by $C_1$–$C_{12}$alkyl, $C_1$–$C_{12}$alkoxy or halogen, unsubstituted $C_6$–$C_{12}$aryl or $C_6$–$C_{12}$aryl which is substituted by halogen, $C_1$–$C_{12}$alkyl or $C_1$–$C_{12}$alkoxy, or a 5- or 6-membered aromatic heterocyclic radical which contains oxygen, sulfur and/or nitrogen and is unsubstituted or substituted by halogen, $C_1$–$C_4$alkyl or $C_1$–$C_4$alkoxy, and $R_2$ and $R_3$ are each independently of the other unsubstituted $C_1$–$C_{18}$alkyl or $C_1$–$C_8$alkyl which is substituted by phenyl, halogen or $C_1$–$C_{12}$alkoxy, $C_2$–$C_6$alkenyl, unsubstituted $C_5$–$C_8$cycloalkyl or $C_5$–$C_8$cycloalkyl which is substituted by $C_1$–$C_{12}$alkyl, $C_1$–$C_{12}$alkoxy or halogen, unsubstituted $C_6$–$C_{12}$aryl or $C_6$–$C_{12}$aryl which is substituted by $C_1$–$C_{12}$alkyl, $C_1$–$C_{12}$alkoxy, $C_2$–$C_{12}$alkoxyalkyl, $C_1$–$C_4$alkylthio or halogen, or a 5- or 6-membered aromatic heterocyclic radical which contains oxygen, sulfur and/or nitrogen and is unsubstituted or substituted by halogen, $C_1$–$C_4$alkyl or $C_1$–$C_4$alkoxy are suitable initiators for the light-induced polymerisation of compounds containing ethylenically unsaturated double bonds.

15 Claims, No Drawings

BISACYLPHOSPHINE SULFIDES

This is a continuation of application Ser. No. 07/925,239, filed on Aug. 4, 1992, now abandoned, which is a continuation of application Ser. No. 07/819,320, filed on Jan. 9, 1992, now abandoned.

The present invention relates to novel bisacylphosphine sulfides, to photocurable compositions which contain these compounds, to the use of bisacylphosphine sulfides as photoinitiators for the photopolymerisation of such compounds containing ethylenically unsaturated double bonds, and to a process for photopolymerising such compounds with bisacylphosphine sulfides as photoinitiators.

Monoacylphosphine sulfides and the use thereof as photoinitiators are disclosed in DE-A-3 034 697.

Bisacylphosphine oxides as initiators for light-induced polymerisation reactions are disclosed in EP-A-184 095. K. Issleib et al. have reported in Z. anorg. allg. Chem. 408,266–274, (1974) on the synthesis of cyclic carbonyl phosphides, as well as on the reaction of 2-phenyl-2-benzophospholene-1,3-dione with sulfur to the corresponding sulfide. The synthesis and spectroscopic data of the cited sulfide are also found in the paper by Andrew R. Barron et al., published in J. Chem. Soc., Chem. Commun. (23), 1753–4, (1987).

It has now been found that bisacylphosphine sulfides are most effective photoinitiators for polymerising compounds containing ethylenically unsaturated double bonds.

Accordingly, the invention relates to compounds of formula I

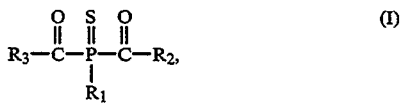

wherein $R_1$ is unsubstituted $C_1$–$C_{18}$alkyl or $C_1$–$C_8$alkyl which is substituted by phenyl, —CN, $C_1$–$C_{12}$alkoxy or halogen, $C_2$–$C_{18}$alkenyl, unsubstituted $C_5$–$C_8$cycloalkyl or $C_5$–$C_8$cycloalkyl which is substituted by $C_1$–$C_{12}$alkyl, $C_1$–$C_{12}$alkoxy or halogen, unsubstituted $C_6$–$C_{12}$aryl or $C_6$–$C_{12}$aryl which is substituted by halogen, $C_1$–$C_{12}$alkyl or $C_1$–$C_{12}$alkoxy, or a 5- or 6-membered aromatic heterocyclic radical which contains oxygen, sulfur and/or nitrogen and is unsubstituted or substituted by halogen, $C_1$–$C_4$alkyl or $C_1$–$C_4$alkoxy, and $R_2$ and $R_3$ are each independently of the other unsubstituted $C_1$–$C_{18}$alkyl or $C_1$–$C_8$alkyl which is substituted by phenyl, halogen or $C_1$–$C_{12}$alkoxy, $C_2$–$C_6$alkenyl, unsubstituted $C_5$–$C_8$cycloalkyl or $C_5$–$C_8$cycloalkyl which is substituted by $C_1$–$C_{12}$alkyl, $C_1$–$C_{12}$alkoxy or halogen, unsubstituted $C_6$–$C_{12}$aryl or $C_6$–$C_{12}$aryl which is substituted by $C_1$–$C_{12}$alkyl, $C_1$–$C_{12}$alkoxy, $C_2$–$C_{12}$alkoxyalkyl, $C_1$–$C_4$alkylthio or halogen, or a 5- or 6-membered aromatic heterocyclic radical which contains oxygen, sulfur and/or nitrogen and is unsubstituted or substituted by halogen, $C_1$–$C_4$alkyl or $C_1$–$C_4$alkoxy.

$R_1$, $R_2$ and $R_3$ as $C_1$–$C_{18}$alkyl may be branched and unbranched alkyl, including methyl, ethyl, propyl, isopropyl, n-butyl, sec-butyl, isobutyl, tert-butyl, pentyl, hexyl, tert-hexyl, heptyl, 2,4,4-trimethylpentyl, octyl, nonyl, decyl, dodecyl, tetradecyl, heptadecyl or octadecyl. $R_1$, $R_2$ and $R_3$ may preferably be $C_1$–$C_{12}$alkyl.

$R_1$, $R_2$ and $R_3$ as $C_1$–$C_8$alkyl which carries one or more, conveniently one to three and, preferably, one or two, substituents, may be benzyl, 1-phenylethyl, 2-phenylethyl, α,α-dimethylbenzyl, 2-methoxyethyl, 2-ethoxyethyl, diethoxymethyl, 2-butoxyethyl, 2-isopropoxyethyl, 2-butoxypropyl, 2-octyloxyethyl, chloromethyl, 2-chloroethyl or trichloromethyl, and are preferably substituted $C_1$–$C_4$alkyl, more particularly benzyl. $R_1$ may also be cyanomethyl, cyanoethyl and the like.

$R_1$ as $C_2$–$C_{18}$alkenyl may be allyl, methallyl, 1,1-dimethylallyl, butenyl, 2-hexenyl, octenyl, undecenyl, dodecenyl or octadecenyl, and is preferably $C_2$–$C_{12}$alkenyl, most preferably $C_2$–$C_6$alkenyl.

$R_2$ and $R_3$ as $C_2$–$C_6$alkenyl may be vinyl, propenyl, butenyl or hexenyl.

$R_1$, $R_2$ and $R_3$ as $C_5$–$C_8$cycloalkyl may be cyclopentyl, cyclohexyl or cyclooctyl, preferably cyclopentyl and cyclohexyl, preferably cyclohexyl. $R_1$, $R_2$ and $R_3$ as substituted $C_5$–$C_8$cycloalkyl, conveniently mono- to tetrasubstituted $C_5$–$C_8$cycloalkyl, may be methylcyclopentyl, dimethylcyclopentyl, methylcyclohexyl, dimethylcyclohexyl, diethylcyclohexyl, methoxycyclopentyl, dimethoxycyclopentyl, ethoxycyclopentyl, diethoxycyclopentyl, methoxycyclohexyl, dimethoxycyclohexyl, ethoxycyclohexyl, diethoxycyclohexyl, chlorocyclohexyl, chlorocyclopentyl, dichlorocyclohexyl or dichlorocyclopentyl. Substituted cycloalkyl is preferably $C_1$–$C_4$alkyl-substituted cycloalkyl.

$R_1$, $R_2$ and $R_3$ as $C_6$–$C_2$aryl may be phenyl, α-naphthyl, β-naphthyl or 4-diphenylyl, preferably phenyl. $R_1$, $R_2$ and $R_3$ as substituted $C_6$–$C_{12}$aryl preferably carry 1 to 3 substituents and may be chlorophenyl, dichlorophenyl, trichlorophenyl, difluorophenyl, tolyl, mesityl, ethylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl or ethoxynaphthyl, preferably dimethoxyphenyl, chlorophenyl and mesityl, preferably dimethoxyphenyl. $R_2$ and $R_3$ as substituted aryl may also be methoxyethylphenyl, ethoxymethylphenyl, methylthiophenyl, isopropylthiophenyl or tert-butylthiophenyl. Alkyl and alkoxy as substituents of aryl contain 1 to 4 carbon atoms and are preferably methyl or methoxy.

A heterocyclic radical $R_1$, $R_2$ and $R_3$ may be mononuclear or polynuclear, preferably mono- or binuclear, typically with a fused benzene ring, and may be furyl, thienyl, pyrrolyl, pyridyl, indolyl, benzoxazolyl, benzimidazolyl or benzothiazolyl. Such a heterocyclic radical preferably contains 4 to 12 carbon atoms. These heterocyclic radicals may carry one or more, conveniently one or two, substituents. Illustrative examples are dimethylpyridyl, methylquinolyl, dimethylpyrrolyl, methoxyfuryl, dimethoxypyridyl or difluoropyridyl.

Halogen is preferably chloro, bromo or fluoro, most preferably chloro.

A preferred embodiment of the invention relates to compounds of formula I, wherein $R_1$ is unsubstituted $C_1$–$C_{12}$alkyl or $C_1$–$C_8$alkyl which is substituted by phenyl, —CN, $C_1$–$C_4$alkoxy or halogen, $C_2$–$C_2$alkenyl, unsubstituted $C_5$–$C_8$cycloalkyl or $C_5$–$C_8$cycloalkyl which is substituted by $C_1$–$C_{12}$alkyl, $C_1$–$C_4$alkoxy or halogen, unsubstituted $C_6$–$C_{12}$aryl or $C_6$–$C_{12}$aryl which is substituted by halogen, $C_1$–$C_{12}$alkyl or $C_1$–$C_4$alkoxy or a 5- or 6-membered aromatic heterocyclic radical which contains oxygen, sulfur and/or nitrogen and is unsubstituted or substituted by halogen, $C_1$–$C_4$alkyl or $C_1$–$C_4$alkoxy, and $R_2$ and $R_3$ are each independently of the other unsubstituted $C_1$-$C_{12}$alkyl or $C_1$-$C_8$alkyl which is substituted by phenyl, halogen or $C_1$-$C_4$alkoxy, $C_2$-$C_6$alkenyl, unsubstituted $C_5$-$C_8$cycloalkyl or $C_5$-$C_8$cycloalkyl which is substituted by $C_1$-$C_{12}$alkyl, $C_1$-$C_4$alkoxy or halogen, unsubstituted $C_6$-$C_{12}$aryl or $C_6$-$C_{12}$aryl which is substituted by $C_1$-$C_{12}$alkyl, $C_1$-$C_4$alkoxy, $C_2$-$C_8$alkoxyalkyl, $C_1$-$C_4$alkylthio or halogen, or a 5- or 6-membered aromatic heterocyclic radical which contains oxygen, sulfur and/or nitrogen and is unsubstituted or substituted by halogen, $C_1$-$C_4$alkyl or $C_1$-$C_4$alkoxy.

Interesting compounds are also those of formula I, wherein $R_1$ is unsubstituted $C_1$-$C_{12}$alkyl or $C_1$-$C_4$alkyl which is substituted by phenyl, —CN, $C_1$-$C_4$alkoxy or halogen, $C_2$-$C_6$alkenyl, or unsubstituted $C_5$-$C_8$cycloalkyl or $C_5$-$C_8$cycloalkyl which is substituted by $C_1$-$C_{12}$alkyl, $C_1$-$C_4$alkoxy or halogen, or unsubstituted $C_6C_{12}$aryl or $C_6C_{12}$aryl which is substituted by halogen, $C_1$-$C_{12}$alkyl or $C_1$-$C_4$alkoxy and $R_2$ and $R_3$ are each independently of the other unsubstituted $C_1$-$C_{12}$alkyl or $C_1$-$C_4$alkyl which is substituted by phenyl, halogen or $C_1$-$C_4$alkoxy, $C_2$-$C_6$alkenyl, or unsubstituted $C_5$-$C_8$cycloalkyl or $C_5$-$C_8$cyclopalkyl which is substituted by $C_1$-$C_{12}$alkyl, $C_1$-$C_4$alkoxy or halogen, or unsubstituted $C_6$-$C_{12}$aryl or $C_6$-$C_{12}$aryl which is substituted by $C_1$-$C_{12}$alkyl, $C_1$-$C_4$alkoxy, $C_2$-$C_8$alkoxyalkyl, $C_1$-$C_4$alkylthio or halogen.

Other preferred compounds of formula I are those wherein $R_1$ is unsubstituted $C_1$-$C_{12}$alkyl, phenyl-$C_1$-$C_4$alkyl, unsubstituted or $C_1$-$C_{12}$alkyl-substituted cyclopentyl or cyclohexyl, or unsubstituted phenyl or phenyl which is substituted by halogen, $C_1$-$C_{12}$alkyl or $C_1$-$C_4$alkoxy, and $R_2$ and $R_3$ are each independently of the other unsubstituted $C_1$-$C_{12}$alkyl, phenyl-$C_1$-$C_4$alkyl, unsubstituted or $C_1$-$C_{12}$alkyl-substituted cyclopentyl or cyclohexyl, or unsubstituted phenyl or phenyl which is substituted by $C_1$-$C_{12}$alkyl, $C_1$-$C_4$alkoxy or halogen.

Also preferred are those compounds of formula I wherein $R_1$ is $C_1$-$C_{12}$alkyl, cyclohexyl or phenyl-$C_1$-$C_4$alkyl, and $R_2$ and $R_3$ are each independently of the other phenyl which is substituted by $C_1$-$C_4$alkoxy, halogen or $C_1$-$C_4$alkyl.

Interesting compounds of formula I are also those wherein $R_2$ and $R_3$ are identical.

Compounds of formula I which also merit interest are those wherein $R_1$ is $C_1$-$C_8$alkyl or benzyl and $R_2$ and $R_3$ are $C_1$-$C_4$alkyl- or $C_1$-$C_4$alkoxy-substituted phenyl.

The compounds of formula I may be prepared by reacting the appropriate phosphines with elemental sulfur:

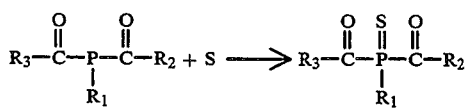

This method is described in DE-A-3 034 697 for the preparation of monoacylphosphine sulfides. The bisacylphosphines are reacted as such or in a suitable inert organic solvent, as in a hydrocarbon such as toluene, cyclohexane or chlorobenzene, or in an aliphatic or aromatic ether, such as dibutyl ether, dioxane, diethylene glycol dimethyl ether or diphenyl ether, with an equimolar amount of elemental sulfur. The resultant bisacylphosphine sulfide, or solution thereof, is freed by filtration from any remaining sulfur. The reaction is conveniently carried out in an inert gas atmosphere, as in nitrogen, argon or carbon dioxide, preferably nitrogen. The reaction temperatures are in the range from 20° to 200° C., preferably from 60° to 120° C., depending on the solvent and the educts. After removal of the solvent, the bisacylphosphine sulfide can be isolated in pure form by distillation or recrystallisation.

The preparation of the bisacylphosphine starting materials is known from the literature to those skilled in the art and is described, for example, in EP-A- 184 095. Thus they may be prepared by reacting a suitable acid halide with a phosphine in the presence of a base, preferably an amine base. The phosphine used in this reaction may conveniently be bis(trimethylsilyl)phenylphosphine. In the reaction with the acid halide, the trimethylsilyl groups are then replaced by the acid radical.

The invention further relates to compositions comprising (a) at least one ethylenically unsaturated photopolymerisable compound and (b) at least one compound of formula I.

In the practice of this invention, the compounds of formula I can be used as photoinitiators for the photopolymerisation of ethylenically unsaturated compounds or mixtures which contain such compounds. Component (a) may suitably be selected from ethylenically unsaturated monomers, oligomers and polymers which react by photopolymerisation to form products of high molecular weight and thereby change their solubility.

The unsaturated compounds may contain one or more olefinic double compounds. They may be low molecular weight compounds (monomers) or high molecular weight compounds (oligomers).

Particularly suitable unsaturated compounds include esters of ethylenically unsaturated carboxylic acids and polyols or polyepoxides, and polymers containing ethylenically unsaturated groups in the chain or in side groups, including unsaturated polyesters, polyamides and polyurethanes and copolymers thereof, polybutadiene and butadiene, polyamides and polyurethanes and copolymers thereof, polybutadiene and butadiene, copolymers, polyisoprene and isoprene copolymers, polymers and copolymers containing (meth)acrylic groups in side-chains, as well as mixtures of one or more such polymers.

Unsaturated carboxylic acids are typically acrylic acid, methacrylic acid, crotonic acid, itaconic acid, cinnamic acid, unsaturated fatty acids, such as linolenic acid or oleic acid. Acrylic acid and methacrylic acid are preferred.

Suitable polyols are aromatic polyols and, preferably, aliphatic and cycloaliphatic polyols. Illustrative examples of aromatic polyols are hydroquinone, 4,4'-dihydroxydiphenyl, 2,2-bis(4-hydroxyphenyl)propane, as well as novolaks and resols. Polyepoxides include those based on the cited polyols, preferably on the aromatic polyols and epichlorohydrin. Further suitable polyols are polymers and copolymers, which contain hydroxyl groups in the polymer chain or in side groups, for example polyvinyl alcohol and copolymers thereof or polymethacrylic hydroxyalkyl esters or copolymers thereof. Other suitable polyols are oligoesters containing hydroxyl end groups.

Illustrative examples of aliphatic and cycloaliphatic polyols are alkylenediols containing preferably 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be esterified partially or completely with one or with different unsaturated carboxylic acids, in which case the free hydroxyl groups of the partial esters may be modified, for example etherified, or esterified with other carboxylic acids.

Illustrative examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentacrylate, dipentaerythritol hexacrylate, tripentaerythritol octacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentacrylate, sorbitol hexacrylate, oligoester acrylates and methacrylates, glycerol di- and -triacrylate, 1,4-cyclohexanediacrylate, bisacrylates and bismethacrylates of polyethylene glycol having molecular weights of 200 to 1500, or mixtures thereof.

Also suitable for use as component (a) are the amides of identical or different unsaturated carboxylic acids of aromatic, cycloaliphatic and aliphatic polyamines containing preferably 2 to 6, more particularly 2 to 4, amino groups. Exemplary of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, bis(β-aminoethyl) ether, diethylenetriamine, triethylenetetramine, bis(β-aminoethoxy)ethane or bis(β-aminopropoxy)ethane. Other suitable polyamines are polymers and copolymers which may contain additional amino groups in the side-chain and oligoamides containing amino end groups.

Exemplary of such unsaturated amides are: methylenebisacrylamide, 1,6-hexamethylenebisacrylamide, diethylenetriaminetrismethacrylamide, bis(methacrylamidopropoxy)ethane, β-methacrylamidoethylmethacrylate, N-[(β-hydroxyethoxy)ethyl]acrylamide.

Suitable unsaturated polyesters and polyamides are derived typically from maleic acid and diols or diamines. Maleic acid can be partially replaced by other dicarboxylic acids. They can be used together with ethylenically unsaturated comonomers, as with styrene. The polyesters and polyamides can also be derived from dicarboxylic acids and ethylenically unsaturated diols or diamines, especially from those with long chains containing typically from 6 to 20 carbon atoms. Polyurethanes are typically those derived from saturated or unsaturated diisocyanates and unsaturated and saturated diols.

Polybutadiene and polyisoprene and copolymers thereof are known. Suitable comonomers include olefins such as ethylene, propene, butene, hexene, (meth)acrylates, acrylonitrile, styrene or vinyl chloride. Polymers containing (meth)acrylate groups in the side-chain are also known. They may typically be reaction products of epoxy resins based on novolak with (meth)acrylic acid, homo- or copolymers of polyvinyl alcohol or their hydroxyalkyl derivatives which are esterified with (meth)acrylic acid or homo- and copolymers of (meth)acrylates which are esterified with hydroxyalkyl(meth)acrylates.

The photopolymerisable compounds can be used by themselves or in any desired mixtures. It is preferred to use mixtures of polyol(meth)acrylates.

Binders may also be added to the compositions of the invention. The addition of binders is particularly useful if the photopolymerisable compounds are liquid or viscous substances. The amount of binder may be from 5–95, preferably 10–90 and, most preferably, 50–90, percent by weight, based on the entire composition. The choice of binder will depend on the field of use and the desired properties therefor, such as the ability of the compositions to be developed in aqueous and organic solvent systems, adhesion to substrates and susceptibility to oxygen.

Suitable binders are typically polymers having a molecular weight of about 5000–2,000,000, preferably 10,000–1,000,000. Illustrative examples are: homo- and copolymers of acrylates and methacrylates, including copolymers of methyl methacrylate/ethyl acrylate/methacrylic acid, poly(alkylmethacrylates), poly(alkylacrylates); cellulose esters and ethers such as cellulose acetate, cellulose acetobutyrate, methyl cellulose, ethyl cellulose; polyvinyl butyral, polyvinyl formal, cyclised rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), polyesters such as poly(ethylene glycol terephthalate) and poly(hexamethylene glycol succinate).

The unsaturated compounds can also be used in admixture with non-photopolymerisable film-forming components. These components may be physically drying polymers or solutions thereof in organic solvents, for example nitrocellulose or cellulose acetobutyrate. They may, however, also be chemically or thermally curable resins such as polyisocynates, polyepoxides or melamine resins. The concurrent use of thermally curable resins is important for the use in so-called hybrid systems which, in a first step, are photopolymerised and, in a second step, crosslinked by a thermal after-treatment.

The photopolymerisable compositions of this invention conveniently contain the photoinitiator (b) in an amount of 0.05 to 15% by weight, preferably of 0.2 to 5% by weight, based on the composition.

The invention also relates to compositions which comprise, in addition to the photoinitiator (b), at least one further photoinitiator and/or other additives.

Further different additives which may be present in the photopolymerisable compositions in addition to the photoinitiator are typically thermal inhibitors which, especially during the preparation of the compositions by mixing the components, prevent premature polymerisation. Such further additives are typically hydroquinone, hydroquinone derivatives, p-methoxyphenol, β-naphthol or sterically hindered phenols, such as 2,6-di(tert-butyl)-p-cresol.

To enhance storage stability in the dark it is possible to add copper compounds, including copper naphthenate, copper stearate or copper octoate, phosphorus compounds, including triphenylphosphine, tributylphosphine, triethyl phosphite, triphenyl phosphite, or tribenzyl phosphite, quaternary ammonium compounds, such as tetramethylammonium chloride or trimethylbenzylammonium chloride, or hydroxylamine derivatives, such as N-diethylhydroxylamine.

The exclusion of atmospheric oxygen during the polymerisation may be effected by adding paraffin or similar wax-like substances which, at the onset of polymerisation, migrate to the surface owing to lack of solubility in the polymer and form a transparent film which prevents air from entering the system.

Minor amounts of UV absorbers, typically those of the benzotriazole, benzophenone or oxanilide type, may be added as light stabilisers. Light stabilisers of the sterically hindered amine type (HALS) can also be added.

In specific cases it can be advantageous to use mixtures of two or more photoinitiators of this invention. Further photoinitiators used in addition to the photoinitiators of formula I may be those selected from the following types: benzophenones, acetophenone derivatives, such as α-hydroxyalkylphenylketones, benzoin alkyl ethers and benzil ketals, or acyl phosphine oxides, bisacylphosphine oxides or titanocenes.

The photopolymerisation can be accelerated, especially in pigmented formulations, by adding amines, such as triethanolamine, N-methyl-diethanolamine, ethyl p-dimethylaminobenzoate or Michler's ketone. The action of the amines can be intensified by the addition of aromatic ketones of the benzophenone type.

The photopolymerisation can further be accelerated by the addition of photosensitisers which shift or broaden the spectral sensitivity. These photosensitisers are preferably aromatic carbonyl compounds such as benzophenone, thioxanthone, anthraquinone and 3-acylcoumarin derivatives as well as 3-(aroylmethylene)-thiazolines.

Depending on the envisaged end use further customary additives are fillers, pigments, dyes, adhesion promoters, wetting agents or levelling agents.

The photopolymerisable compositions can be used for a variety of purposes, including their use in printing ink compositions, in clear coating formulations, in white enamels, in paints, in paints for exterior coatings, and for photographic reproduction processes, for image recording processes or for the production of printing plates, for making three-dimensional objects, as by stereolithography or mass hardening, as dental filling compositions, as adhesives, as coatings for optical fibres, for printed electronic circuits or for coating electronic components.

In coating formulations there are frequently used two-component mixtures of a prepolymer with a polyunsaturated monomer or three-component mixtures which contain an additional mono-unsaturated monomer. The prepolymer primarily determines the properties of the coat and, by varying it, the skilled person can influence the properties of the cured film. The polyunsaturated monomer acts as crosslinker which makes the coating film insoluble. The mono-unsaturated monomer acts as reactive diluent with the aid of which the viscosity is lowered without having to use a solvent.

Two- and three-component systems based on a prepolymer are used for printing inks as well as for coating compositions, photoresists or other photocurable compositions. Single component systems based on photocurable prepolymers are also often used as binders for printing inks.

Unsaturated polyester resins are normally used together with a mono-unsaturated monomer, preferably with styrene. Specific single component systems are often used for photoresists, for example the polymaleimides, polychalcones or polyimides disclosed in DE-OS 2 308 830.

The photocurable compositions of this invention may suitably be used as coating compositions for substrates of all kinds, such as wood, paper, ceramics, synthetic resins such as polyesters and cellulose acetate films, and metals such as copper and aluminium, to which it is desired to apply a protective layer or an image by photopolymerisation.

The substrate can be coated by applying to said substrate a liquid composition, a solution or suspension. This is done typically by dip-coating, brushing, spraying or reverse roller coating. The add-on (layer thickness) and the nature of the substrate (support) will depend on the desired field of application. Suitable substrates for recording photographic information are sheets of polyester, cellulose acetate or resin-coated papers. Specially treated aluminium is used for offset printing formes, and copper-clad laminates for making printed circuit boards. The layer thicknesses for photographic materials and offset printing formes are normally about 0.5 to about 10 μm. If solvents are concurrently used, these can be removed after coating.

Photocuring is of great importance for printing inks, as the drying time of the binder is a decisive factor in the rate of production of graphic products and should be in the order of fractions of seconds. UV curable printing inks are of particular importance for screen printing.

The photocurable compositions of this invention are also very suitable for making printing plates. For this utility mixtures of soluble linear polyamides or styrene/butadiene rubber with photopolymerisable monomers, typically acrylamides, and a photoinitiator, are used. Films and plates of these systems (wet or dry) are exposed via the negative (or positive) of the original and the non-cured parts are subsequently eluted with a solvent.

A further field of use of photocuring is metal coating, as in the coating of sheet metal and tubes, cans or bottle caps, as well as the photocuring of resin coatings, for example PVC floor or wall coverings.

Illustrative of the photocuring of paper coatings is the colourless coating of labels, record sleeves or book jackets.

The use of photocurable compositions is also important for imaging techniques and for the optical production of information carriers. For these utilities, the layer (wet or dry) applied to the substrate is irradiated through a photomask with shortwave light and the unexposed areas of the layer are removed by treatment with a solvent (=developer). The application of the photocurable layer can also be effected by electrodeposition on metal. The exposed areas are crosslinked-polymeric and hence insoluble and remain on the substrate. Visible images are formed by appropriate colouration. If the substrate is a metallised layer, then the metal can be etched away after exposure and development at the unexposed areas or reinforced by galvanising. In this manner it is possible to make printed circuit boards and photoresists.

The invention further relates to a process for photopolymerising monomeric, oligomeric or polymeric compounds containing at least one ethylenically unsaturated double bond, which comprises adding to said compounds a compound of formula I and irradiating with light of wavelengths in the range from 200 to 600 nm.

Polymerisation is carried out by known methods of photopolymerisation by irradiation with sunlight or with light which is rich in shortwave radiation. Suitable light sources are typically mercury medium-pressure, high-pressure and low-pressure lamps, superactinic fluorescent tubes, metal halide lamps or lasers the maximum emissions of which are in the range from 250–450 nm. Laser light sources have the advantage that no photomasks are necessary, as the controlled laser beam writes direct onto the photocurable layer. Where combinations with photosensitisers are used, it is also possible to use light of longer wavelength or laser beams of up to 600 nm.

The compositions are conveniently prepared by mixing the individual components.

The invention further relates to a cured composition which is obtained by the above described process.

The bisacylphosphine sulfide photoinitiators of this invention have good solubility in conventional, preferably apolar, resins such as silicones.

A further advantage is the insignificant yellowing of the compositions cured with the inventive photoinitiators.

The invention is described in more detail by the following Examples in which and throughout the remainder of the description and in the claims, parts and percentages are by weight, unless otherwise indicated.

EXAMPLE 1

Bis(2,6-dimethoxybenzoyl)-(2-methylpropyl)phosphine sulfide a) Bis(2,6-dimethoxybenzoyl)-(2-methylpropyl)phosphine A mixture of 5 ml (0.0425 mol) of (2-methylpropyl)phosphine and 13 ml (0.0935 mol) of triethylamine is added dropwise at 100°–110° C. over 30 minutes to 18.8 g (0.0935 mol) of 2,6-dimethoxybenzoyl chloride in 100 ml of toluene. The reaction is brought to completion by stirring the reaction mixture at the same temperature for 6 hours, whereupon the product, as well as triethylammonium chloride, fall out as a yellowish precipitate. After cooling the reaction mixture, the ammonium salt is dissolved by addition of water and the product is isolated by filtration and dried under vacuum, affording 11.1 g (62.5% of theory) of the title compound in the form of a white powder with a melting point of 138°–140° C.

| Elemental analysis: | C | calcd: | 63.15% | H | calcd: | 6.50% |
|---|---|---|---|---|---|---|
| | | found | 63.19% | | found: | 6.52% | b) Bis(2,6-dimethoxybenzoyl)-(2-methylpropyl)phosphine sulfide 10.0 g (0.024 tool) of bis(2,6-dimethoxybenzoyl)-(2-methylpropyl)phosphine are added to toluene and the mixture is heated to 60° C. while introducing nitrogen, whereupon the educt dissolves completely. Then 0.8 g (0.024 tool) of sulfur are added at 60° C. The reaction mixture is thereafter stirred for 6 hours, cooled, and concentrated under vacuum. The residue is recrystallised from ethyl acetate, affording 6.9 g (63.9% of theory) of the title compound in the form of a yellow powder with a melting point of 145°–147° C.

| Elemental analysis: | calcd: | C | 58.66% | found: | C | 58.59% |
|---|---|---|---|---|---|---|
| | | H | 6.04% | | H | 6.01% |
| | | S | 7.12 | | S | 7.03% |

EXAMPLES 2–3

The compounds of Examples 2 and 3 are prepared using the appropriate starting phosphines in accordance with the general procedure described in Example 1.

| Elemental analysis: | calcd: | C | 58.66% | found: | C | 58.59% |
|---|---|---|---|---|---|---|
| | | H | 6.04% | | H | 6.01% |
| | | S | 7.12% | | S | 7.03% |

TABLE 1

OCH₃     CH₃O $$\text{Structure with } O=C-P(R_1)-C=O \text{, P=S, flanked by two 2,6-dimethoxyphenyl groups}$$

OCH₃     CH₃O

| Example | R₁ | Melting Point [°C.] | Elemental analysis [%] calcd. / found | | |
|---|---|---|---|---|---|
| | | | C | H | S |
| 2 | —CH(CH₃)—CH₂—CH₃ | 117–118 | 58.66 / 58.48 | 6.04 / 6.04 | 7.12 / 7.30 |
| 3 | —CH₂— 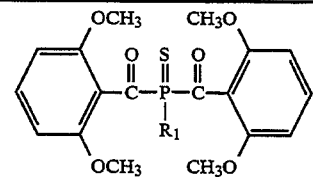 (phenyl) | 138–139 | 61.98 / 61.88 | 5.20 / 5.25 | 6.62 / 6.83 |

EXAMPLE 4

Initiator activity in a white enamel formulation

A photopolymerisable composition comprising the following ingredients is prepared: (the parts are parts by weight)

13.5 parts of ®Ebercryl 830 (polyester acrylate, UCB, Belgium)

0.5 part of trimethylolpropane trisacrylate (Degussa)

1 part of 1,6-hexanediol diacrylate (Röhm)

5.0 parts of titanium dioxide (rutile type; ®R-TC2 Tioxide, France)

To this composition is added the amount of test photoinitiator given in Table 2. The formulation is applied in a layer thickness of 100 μm to aluminium sheets. The samples are then irradiated in a PPG exposure apparatus with mercury medium-pressure lamps (2×80 W/cm). The sample is passed under the lamps on a belt moving at a speed of 10 m/min for as often as is necessary to obtain a wipe-resistant coating surface. The fewer the number of passes (n), the higher the reactivity of the tested compound. The hardness of the sample is determined by means of the pendulum hardness test using the apparatus of König (DIN 53 157). The greater the number of seconds, the harder the tested sample. The yellowing of the sample is determined by measuring the Yellowness Index (YI) in accordance with ASTM D 1925-70. The lower the value, the lesser the yellowing of the sample. The pendulum hardness and the yellowing are determined immediately after the cure and after an additional exposure for 15 minutes and 16 hours under 4 40 W Philips TL 40/03 lamps. The gloss of the sample is measured in accordance with ASTM D 523 at an angle of incidence of 20° and 60° after an additional exposure of 15 minutes and 16 hours. The degree of reflected light is given in %. The higher the values, the better the gloss. The results are summarised in Table 2.

TABLE 3

| Reactivity | Pendulum hardness [s] | | | YI | | | Glass 20/60° [in %] | |
| --- | --- | --- | --- | --- | --- | --- | --- | --- |
| [n × 10 m/min] | immed. | 15 min | 16 h | immed. | 15 min | 16 h | 15 min | 16 h |
| 2 | 102 | 139 | 167 | 2.7 | 1.5 | 2.4 | 23/66 | 15/59 |

TABLE 2

| Compound of Example [wt. %] | Reactivity [n × 10 m/min] | Pendulum hardnes [s] | | | YI | | | Gloss 20/60° [in %] |
| --- | --- | --- | --- | --- | --- | --- | --- | --- |
| | | immed. | 15 min | 16 h | immed. | 15 min | 16 h | |
| 1% Ex. 1 b | 6 | 106 | 157 | 181 | 1.7 | 0.3 | −0.3 | 65/86 |
| 2% Ex. 1 b | 4 | 125 | 160 | 193 | 3.3 | 0.4 | −0.2 | 78/90 |

EXAMPLE 5

Initiator reactivity in a white enamel formulation

A photopolymerisable composition comprising the following ingredients is prepared:
 30% of ®Ebecryl 608 (epoxy acrylate, ex UCB, Belgium)
 15% of trimethylolpropane trisacrylate
 5% of N-vinylpyrrolidone
 50% of titanium dioxide (rutile type; ®R-TC2; Tioxide, France)

Two percent by weight of the photoinitiator of Example 1b) is incorporated in this formulation. The formulation is applied in a layer thickness of 100 μm to an aluminium sheet. The 100 μm layer is cured by irradiation with a Hanovia mercury medium-pressure lamp (80 W/cm). The sample is passed under the lamps on a belt moving at a speed of 10 m/min for as often as is necessary to obtain a wipe-resistant coating surface. The fewer the number of passes (n), the higher the reactivity of the tested compound. The hardness of the sample is determined by means of the pendulum hardness test using the apparatus of König (DIN 53 157). The greater the number of seconds, the harder the tested sample. The yellowing of the sample is determined by measuring the Yellowness Index (YI) in accordance with ASTM D 1925-70. The lower the value, the lesser the yellowing of the sample. The pendulum hardness and the yellowing are determined immediately after the cure and after an additional exposure for 15 minutes and 16 hours under 4 40 W Philips TL 40/03 lamps. The gloss of the sample is measured in accordance with ASTM D 523 at an angle of incidence of 20° and 60° after an additional exposure of 15 minutes and 16 hours. The degree of reflected light is given in %. The higher the value, the better the gloss. The results are summarised in Table 3.

What is claimed is:

1. A compound of formula I

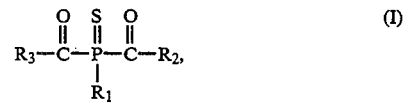

wherein $R_1$ is unsubstituted $C_1$-$C_{18}$alkyl or $C_1$-$C_8$alkyl which is substituted by phenyl, —CN, $C_1$-$C_{12}$alkoxy or halogen, $C_2$-$C_{18}$alkenyl, unsubstituted $C_5$-$C_8$cycloalkyl or $C_5$-$C_8$cycloalkyl which is substituted by $C_1$-$C_{12}$alkyl, $C_1$-$C_{12}$alkoxy or halogen, unsubstituted $C_6$-$C_{12}$aryl or $C_6$-$C_{12}$aryl which is substituted by halogen, $C_1$-$C_{12}$alkyl or $C_1$-$C_{12}$alkoxy, or a 5- or 6-membered aromatic heterocyclic radical which contains oxygen, sulfur and/or nitrogen and is unsubstituted or substituted by halogen, $C_1$-$C_4$alkyl or $C_1$-$C_4$alkoxy, and $R_2$ and $R_3$ are each independently of the other unsubstituted $C_1$-$C_{18}$alkyl or $C_1$-$C_8$alkyl which is substituted by phenyl, halogen or $C_1$-$C_{12}$alkoxy, $C_2$-$C_6$alkenyl, unsubstituted $C_5$-$C_8$cycloalkyl or $C_5$-$C_8$cycloalkyl which is substituted by $C_1$-$C_{12}$alkyl, $C_1$-$C_{12}$alkoxy or halogen, unsubstituted $C_6$-$C_{12}$aryl or $C_6$-$C_{12}$aryl which is substituted by $C_1$-$C_{12}$alkyl, $C_1$-$C_{12}$alkoxy, $C_2$-$C_{12}$alkoxyalkyl, $C_1$-$C_4$alkylthio or halogen, or a 5- or 6-membered aromatic heterocyclic radical which contains oxygen, sulfur and/or nitrogen and is unsubstituted or substituted by halogen, $C_1$-$C_4$alkyl or $C_1$-$C_4$alkoxy.

2. A compound according to claim 1, wherein $R_1$ is unsubstituted $C_1$-$C_{12}$alkyl or $C_1$-$C_8$alkyl which is substituted by phenyl, —CN, $C_1$-$C_4$alkoxy or halogen, $C_2$-$C_{12}$alkenyl, unsubstituted $C_5$-$C_8$cycloalkyl or $C_5$-$C_8$cycloalkyl which is substituted by $C_1$-$C_{12}$alkyl, $C_1$-$C_4$alkoxy or halogen, unsubstituted $C_6$-$C_{12}$aryl or $C_6$-$C_{12}$aryl which is substituted by halogen, $C_1$-$C_{12}$alkyl or $C_1$-$C_4$alkoxy, or a 5- or 6- membered aromatic heterocyclic radical which contains oxygen, sulfur and/or nitrogen and is unsubstituted or substituted by halogen, $C_1$-$C_4$alkyl or $C_1$-$C_4$alkoxy, and $R_2$ and $R_3$ are each independently of the other unsubstituted $C_1$-$C_{12}$alkyl or $C_1$-$C_8$alkyl which is substituted by phenyl, halogen or $C_1$-$C_4$alkoxy, $C_2$-$C_6$alkenyl, unsubstituted $C_5$-$C_8$cycloalkyl or $C_5$-$C_8$cycloalkyl which is substituted by $C_1$-$C_{12}$alkyl, $C_1$-$C_4$alkoxy or halogen, unsubstituted $C_6$-$C_{12}$aryl or $C_6$-$C_{12}$aryl which is substituted by $C_1$-$C_1$-

$C_1$–$C_{12}$alkyl, $C_1$–$C_4$alkoxy, $C_2$–$C_8$alkoxyalkyl, $C_1$–$C_4$alkylthio or halogen, or a 5- or 6-membered aromatic heterocyclic radical which contains oxygen, sulfur and/or nitrogen and is unsubstituted or substituted by halogen, $C_1$–$C_4$alkyl or $C_1$–$C_4$alkoxy.

3. A compound according to claim 2, wherein $R_1$ is unsubstituted $C_1$–$C_{12}$alkyl or $C_1$–$C_4$alkyl which is substituted by phenyl, —CN, $C_1$–$C_4$alkoxy or halogen, $C_2$–$C_6$alkenyl, or unsubstituted $C_5$–$C_8$cycloalkyl or $C_5$–$C_8$cycloalkyl which is substituted by $C_1$–$C_{12}$alkyl, $C_1$–$C_4$alkoxy or halogen, or unsubstituted $C_6$–$C_{12}$aryl or $C_6$–$C_{12}$aryl which is substituted by halogen, $C_1$–$C_{12}$alkyl or $C_1$–$C_{12}$alkoxy, and $R_2$ and $R_3$ are each independently of the other unsubstituted $C_1$–$C_{12}$alkyl or $C_1$–$C_4$alkyl which is substituted by phenyl, halogen or $C_1$–$C_4$alkoxy, $C_2$–$C_6$alkenyl, or unsubstituted $C_5$–$C_8$cycloalkyl or $C_5$–$C_8$cycloalkyl which is substituted by $C_1$–$C_{12}$alkyl, $C_1$–$C_4$alkoxy or halogen, or unsubstituted $C_6$–$C_{12}$aryl or $C_6$–$C_{12}$aryl which is substituted by $C_1$–$C_{12}$alkyl, $C_1$–$C_4$alkoxy, $C_2$–$C_8$alkoxyalkyl, $C_1$–$C_4$alkylthio or halogen.

4. A compound according to claim 3, wherein $R_1$ is unsubstituted $C_1$–$C_{12}$alkyl, phenyl-$C_1$–$C_4$alkyl, unsubstituted or $C_1$–$C_{12}$alkyl-substituted cyclopentyl or cyclohexyl, or unsubstituted phenyl or phenyl which is substituted by halogen, $C_1$–$C_{12}$alkyl or $C_1$–$C_4$alkoxy, and $R_2$ and $R_3$ are each independently of the other unsubstituted $C_1$–$C_{12}$alkyl, phenyl-$C_1$–$C_4$alkyl, unsubstituted or $C_1$–$C_{12}$alkyl-substituted cyclopentyl or cyclohexyl, or unsubstituted phenyl or phenyl which is substituted by $C_1$–$C_{12}$alkyl, $C_1$–$C_4$alkoxy or halogen.

5. A compound according to claim 4, wherein $R_1$ is $C_1$–$C_{12}$alkyl, cyclohexyl or phenyl-$C_1$–$C_4$alkyl, and $R_2$ and $R_3$ are each independently of the other phenyl which is substituted by $C_1$–$C_4$alkoxy, halogen or $C_1$–$C_4$alkyl.

6. A compound according to claim 1, wherein $R_1$ is $C_1$–$C_8$alkyl or benzyl, $R_2$ and $R_3$ are $C_1$–$C_4$alkyl- or $C_1$–$C_4$alkoxy-substituted phenyl.

7. A composition comprising (a) at least one ethylenically unsaturated photopolymerisable compound and (b) at least one compound of formula I according to claim 1.

8. A composition according to claim 7 which, in addition to the photoinitiator (b), comprises at least one further photoinitiator and/or other additives.

9. A composition according to claim 7 comprising 0.05 to 15% by weight of component b), based on said composition.

10. A composition according to claim 9 comprising 0.2 to 5% by weight, of component b), based on said composition.

11. A process for photopolymerising compounds containing ethylenically unsaturated double bonds, which comprises irradiating a composition as claimed in claim 8 with light in the range from 200 to 600 nm.

12. A process according to claim 11 for the preparation of coating compositions, composites, printing plates, photoresists for electronic printed circuits, adhesives or coatings for optical fibres.

13. A process according to claim 11, which is carried out according to the method of mass curing or stereolithography.

14. A cured composition obtained by the process as claimed in claim 11.

15. A compound according to claim 1 wherein $R_2$ and $R_3$ are identical.

* * * * *